United States Patent [19]

Guhl et al.

[11] Patent Number: 4,657,867
[45] Date of Patent: Apr. 14, 1987

[54] MULTIWELL TISSUE CULTURE ASSEMBLY WITH FEATURES FOR REDUCED MEDIA EVAPORATION

[75] Inventors: T. Andrew Guhl, Oxnard; Luther R. Johnson, Thousand Oaks, both of Calif.

[73] Assignee: Becton, Dickinson and Company, Franklin Lakes, N.J.

[21] Appl. No.: 667,319

[22] Filed: Nov. 1, 1984

[51] Int. Cl.[4] .................. C12M 3/00; C12M 1/20; B65D 51/16

[52] U.S. Cl. .................................. 435/284; 435/301; 220/366

[58] Field of Search ............... 435/284, 285, 286, 297, 435/298, 299, 300, 301, 810; 220/366, 356, 352; 215/307

[56] References Cited

U.S. PATENT DOCUMENTS

| | | | |
|---|---|---|---|
| 3,107,204 | 10/1963 | Brown et al. | 435/33 |
| 3,597,326 | 8/1971 | Liner | 435/298 |
| 3,649,464 | 3/1972 | Freeman | 435/284 |
| 4,010,078 | 3/1977 | Taylor | 435/38 |
| 4,012,288 | 3/1977 | Lyman et al. | 435/301 X |
| 4,038,149 | 7/1977 | Liner et al. | 435/300 |
| 4,321,330 | 3/1982 | Baker et al. | 435/299 X |
| 4,349,632 | 9/1982 | Lyman et al. | 435/284 |
| 4,358,908 | 11/1982 | Song | 47/66 |

Primary Examiner—Robert J. Warden
Assistant Examiner—Randall E. Deck
Attorney, Agent, or Firm—Richard J. Rodrick; John L. Voellmicke

[57] ABSTRACT

A multiwell tissue culture assembly comprises a plate and a lid. The plate includes a plurality of wells for receiving liquids therein. Upstanding side walls form the outside border of the plate. A ledge is spaced inwardly of the side walls and extends around the plate between the side walls and the wells. The lid is removably positioned on the plate and includes a substantially planar cover extending over the wells. A labyrinth passage is associated with the cover, the side walls, the ledge and the wells to permit air exchange between the wells and the external environment to maintain equalibration therebetween, but to partially prevent air entrance to the wells to minimize evaporation of liquids in the wells.

9 Claims, 5 Drawing Figures

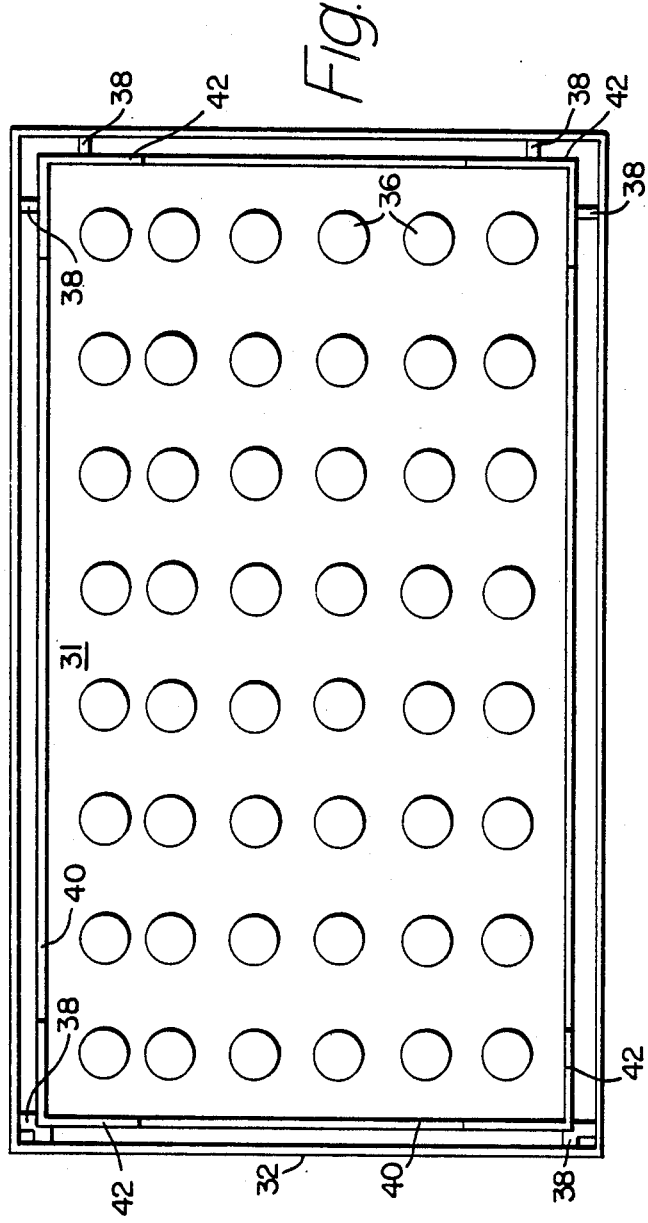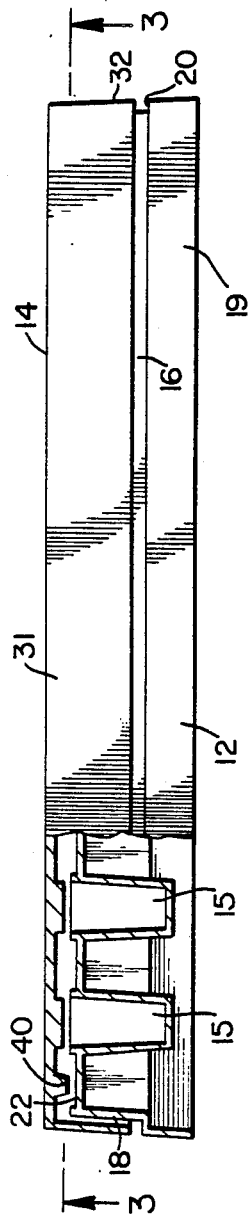

MULTIWELL TISSUE CULTURE ASSEMBLY WITH FEATURES FOR REDUCED MEDIA EVAPORATION

BACKGROUND OF THE INVENTION

1. Field of the Invention

The present invention relates to a tissue culture device, and more particularly, concerns a multiwell tissue culture assembly for in vitro cultivation of cells in growth media, with features to reduce the media evaporation during use.

2. Description of the Prior Art

Tissue culture assemblies, frequently referred to as tissue culture plates, are commonly used for in vitro cultivation of cells particularly for experimental purposes. Multiwell tissue culture plates have been used for these purposes, and include six, twelve, twenty-four, forty-eight and ninety-six wells. Such multiwell tissue culture plates are convenient for the investigator in order to conduct tests for the separation of individual cell cultures while maintaining the cultures in close proximity (all in one plate with a single lid) for performance of related tests or assays on all the cultures.

Presently known and available lids for covering multiwell tissue culture plates have been designed to serve at least three purposes: (1) maintenance of sterility of the contents within the wells, (2) elimination of well-to-well cross contamination due to vapor condensation on the lid undersurfaces, and (3) maintenance of adequate atmospheric ventilation or air exchange between well interiors and the external environment. While the first two of the aforementioned purposes have been served well by current multiwell tissue culture plate lids, the last mentioned feature has not been adequately provided. Specifically, currently available lids for multiwell tissue culture plates permit too much air to flow to the wells from the external environment. In a larger multiwell tissue culture plate, such air exchange generally causes no problems with respect to the media and cell cultures in the interior wells. However, those wells around the periphery or the corners of the tissue culture plate are disturbed by excess airflow from the external environment. Excess air causes the evaporation of cell culture media, resulting in a concentration of media constituents. As a result, in the peripheral and corner wells, osmolarity of the media is not in balance with cellular protoplasm. Consequently, cell growth is retarded in those wells where media evaporation has occurred due to this excessive air exchange. Media must either be replenished more frequently to compensate for evaporation, or the peripheral or corner wells are not used for the cell culturing procedures.

Multiwell tissue culture assemblies are exemplified in U.S. Pat. Nos. 4,349,632; 4,038,149; 4,012,288; 4,010,078; 3,597,326 and 3,107,204. Another culture vessel is exemplified in U.S. Pat. No. 4,358,908. None of the inventions described in the above-listed patents overcomes the problem of media evaporation due to excessive air exchange between the wells and the external environment.

Accordingly, there is still a need for a multiwell tissue culture assembly which is capable of reducing the air flowing to the wells, so as to cause a reduction in evaporation of media in the wells, while maintaining sufficient air flow to allow equilibration between culture media in the wells and atmospheric conditions external to the multiwell tissue culture assembly. The present invention is directed to such a multiwell tissue culture assembly which solves the above-described problems.

SUMMARY OF THE INVENTION

The multiwell tissue culture assembly of the present invention comprises a plate and a lid. The plate includes a plurality of wells for receiving liquids therein. Upstanding side walls form the outside border of the plate. A ledge is spaced inwardly of the side walls and extends around the plate between the side walls and the wells. The lid is removably positioned on the plate and includes a substantially planar cover extending over the wells. Means associated with the cover, the side walls, the ledge and the wells permits air exchange between the wells and the external environment to maintain equilibration therebetween, but to partially prevent air entrance to the wells to minimize evaporation of liquids in the wells.

In a preferred embodiment of the present invention, the lid includes a skirt which surrounds the cover and extends downwardly in spaced relation with respect to the side walls of the plate. A rib is inwardly spaced from the skirt and extends downwardly from the cover into a recess formed in the ledge. The rib, however, is out of contact, but in spaced relation with respect to the recessed ledge. A flange extends downwardly from each corner of the cover as a longer extension of the rib in the corners. These flanges contact the recessed ledge of the plate so that the cover is raised in spaced relation over the openings into the wells. During use of this multiwell tissue culture assembly, the spaces formed by the foregoing elements form a labyrinth passage which permits an air exchange between the wells and the external environment. In conjunction with the flanges, the labyrinth passages causes a partial blockage of air exchange with respect to the wells thereby minimizing evaporation of media in the wells.

In accordance with the principles of the present invention, significant improvements over currently known and available multiwell tissue culture assemblies are provided. Most importantly, the present invention eliminates or substantially reduces the problem of excessive media evaporation that occurs in multiwell tissue culture plates and lids of current design. While the present invention affords this new feature, the other main purposes of the lid are not compromised. In particular, the present invention also maintains sterility of the contents in the multiwell plate and allows adequate gaseous exchange to occur between the wells and the external environment. Media loss, particularly in the corner or peripheral wells, may be reduced by up to fifty percent of the loss exhibited in current multiwell plate configurations. Accordingly, the present invention optimizes conditions for cell culturing procedures.

BRIEF DESCRIPTION OF THE DRAWINGS

FIG. 2 is a side elevational view of the multiwell tissue culture assembly as assembled, with a partial sectional view of one corner thereof;

FIG. 3 is a cross-sectional view of the lid of the multiwell tissue culture assembly taken along line 3—3 of FIG. 2;

DETAILED DESCRIPTION

Figure 1:
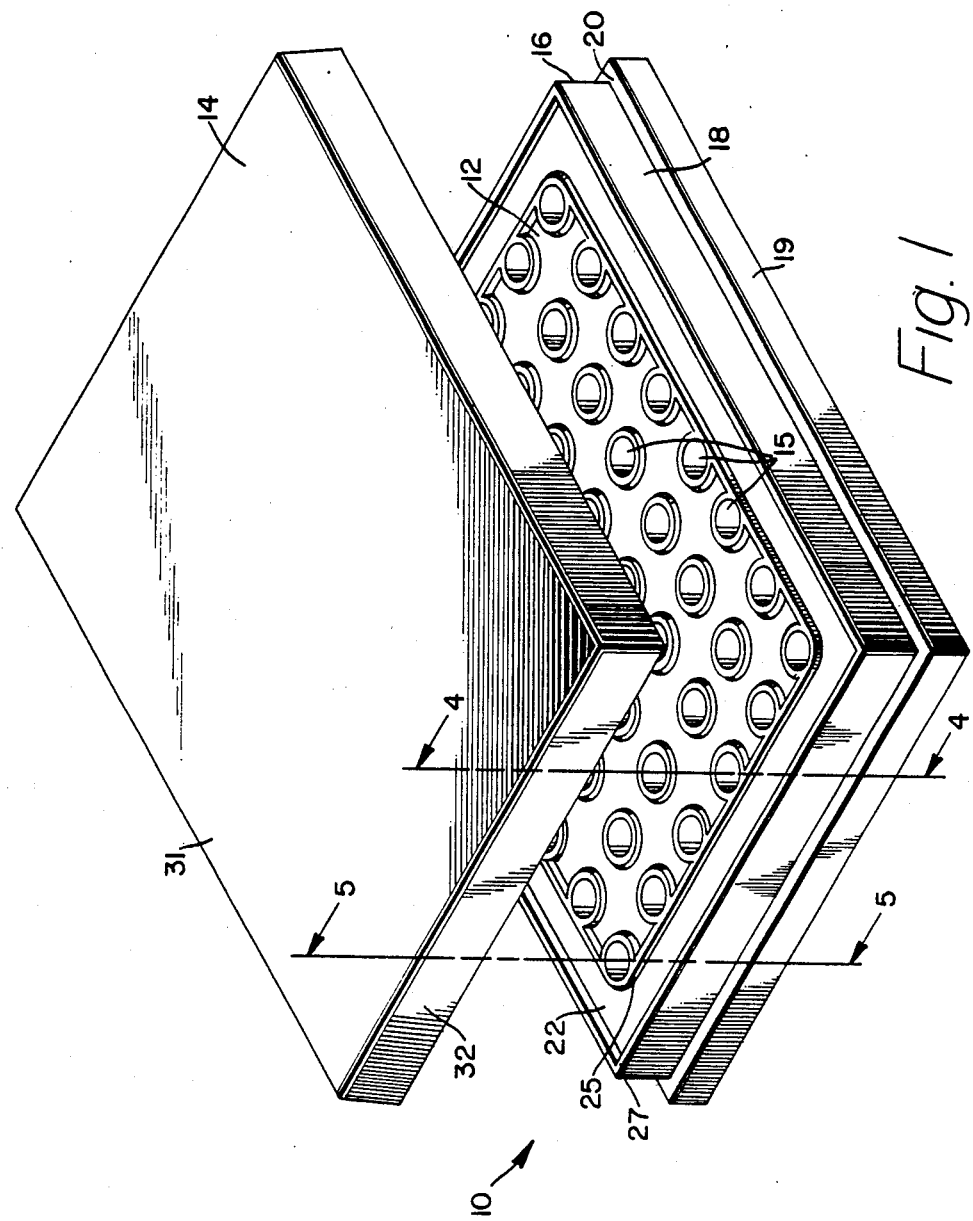
FIG. 1 is a perspective view of one embodiment of the multiwell tissue culture assembly of the present invention illustrating the lid removed from the plate.

While this invention is satisfied by embodiments in many different forms, there is shown in the drawings and will hereinafter be described in detail a preferred embodiment of the invention with the understanding that the present disclosure is to be considered as exemplary of the principles of the invention and is not intended to limit the invention to the embodiment illustrated. The scope of the invention will be measured by the appended claims and their equivalents.

Referring now to the drawings, there is illustrated a representative embodiment of the multiwell tissue culture assembly 10 of the present invention. Assembly 10 includes two main components: a plate 12 and a lid 14.

Turning first to plate 12, it can be seen in the embodiment being described that it is a multiwell plate having a plurality of wells 15 for the receipt of liquids 13 therein. Such liquids may be liquid cell culture media serving as a growth environment for cell culture procedures. There may be any number of wells 15 in plate 12, although six, twelve, twenty-four, forty-eight and ninety-six well plates are commonly known and available. In FIG. 1, a forty-eight well plate is illustrated, merely for exemplary purposes. Most standard multiwell plates have the wells arranged in orthogonal rows and columns so as to be able to clearly identify the individual wells being used. Of course, the arrangement of the wells in plate 12 is not an essential limitation of the present invention, since any arrangement of wells is contemplated by the invention.

Surrounding the wells and forming the outside border of plate 12 are side walls 16. In the present embodiment, the plate is in the shape of a rectangle so that there are four side walls 16. In most instances, well known tissue culture plates are quadrilaterally shaped, although for purposes of the present invention the plate may be fabricated in any practicable configuration. Side walls 16 include and upper portion 18 and a lower portion 19. It can be seen that lower portion 19 of the side walls is stepped from upper portion 18 of the side walls to form an annular shoulder 20 between the upper and lower portions. Lower portion 19 serves as an annular base for plate 12 when the present multiwell tissure culture assembly is being used.

Figure 4:
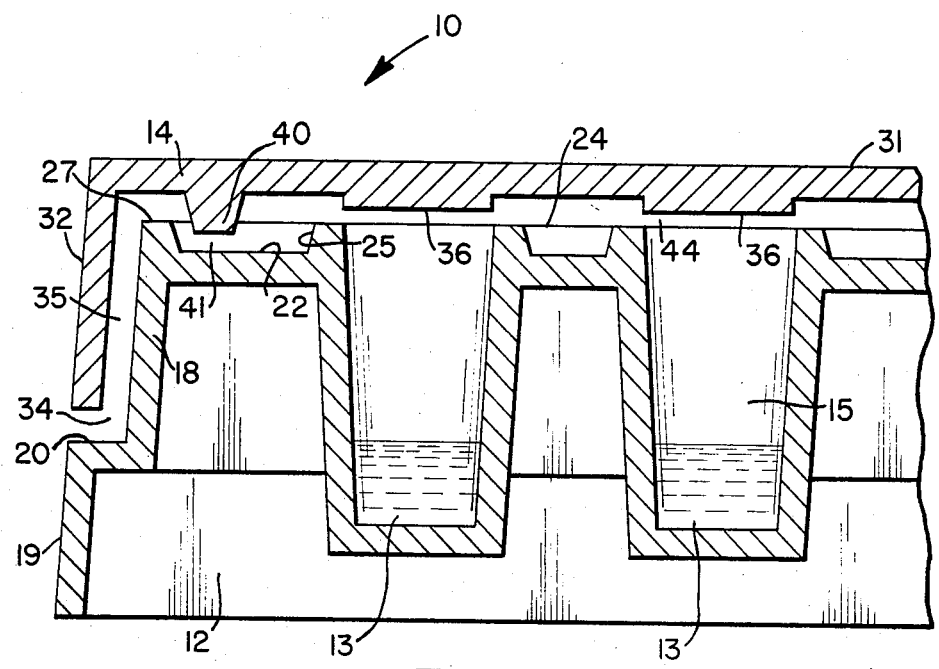
FIG. 4 is an enlarged, partial sectional view of the lid and plate arrangement taken along line 4—4 of FIG. 1, with the lid assembled to the plate.
Figure 5:
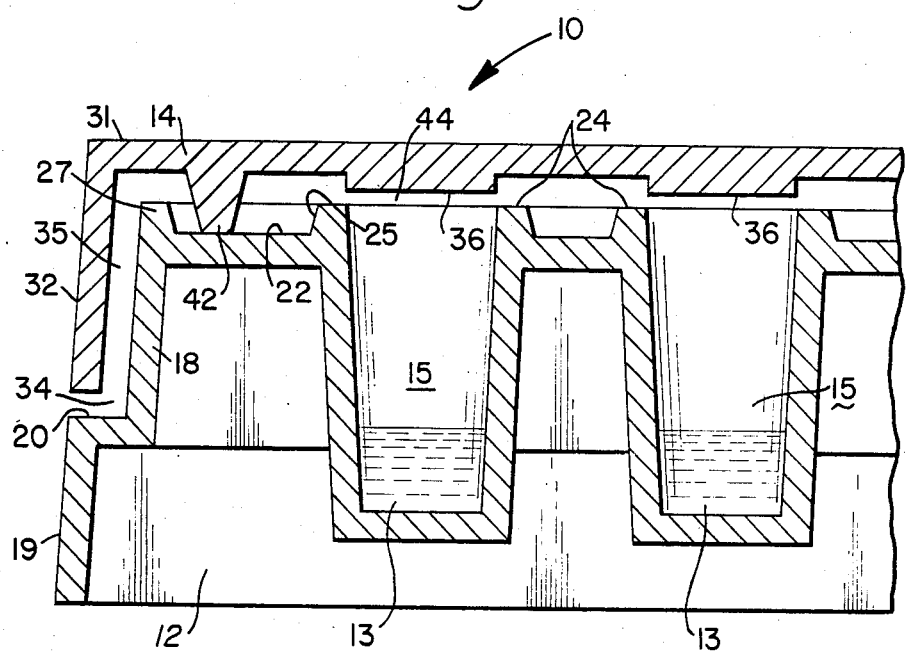
FIG. 5 is an enlarged, partial sectional view of the lid and plate arrangement taken along line 5—5 of FIG. 1, with the lid assembled to the plate.

Spaced inwardly of the upper portion of the side walls and around the upper surface of plate 12 is a recessed ledge 22, as seen more clearly in FIGS. 4 and 5, taken in conjunction with FIGS. 1 and 2. Ledge 22 thereby forms a border around the wells in the interior of plate 12. As illustrated in the drawings, ledge 22 is recessed below the level of the openings 24 into wells 15. Typically, the openings into the wells are all in the same substantially horizontal plane extending along a top surface of the multiwell plate. Recessed ledge 22 is defined by two upstanding rims 25 and 27 with rim 25 being internally located, while rim 27 represents the top segment of upper portion 18 of the side walls which extends to a position raised above the recessed ledge. While ledge 22 is illustrated as being flat and substantially in the horizontal plane, it is understood that the ledge may be a notch, such as a v-shape, or may be a smoothly curved shape, or other desirable configurations.

Lid 14 is a separate, removable member which covers all of the wells in the multiwell plate. Although lid 14 is illustrated in all of the drawing figures, the details of lid 14 are best illustrated in FIGS. 3,4 and 5. Lid 14 includes a substantially planar cover 31 large enough to extend over all of the wells in the multiwell plate. The shape of cover 31 is compatible with the shape of plate 12. Extending around cover 31 is a downwardly depending skirt 32 which forms a border around lid 14. Skirt 32 has four sides, each of which extends downwardly substantially parallel to an adjacent side wall of the multiwell plate. When lid 14 is positioned over plate 12, skirt 32 terminates in a position adjacent to, but out of contact with, shoulder 20 of the multiwell plate thereby leaving a space 34 therebetween. Moreover, it can be seen that skirt 32 also leaves a space 35 between itself and upper portion 18 of the side walls of the multiwell plate.

A plurality of rings 36, in the form of small protuberances, is formed on the underside of cover 31. Each ring 36 is adapted to overlie each opening 24 of the wells so as to contribute to the isolation of each well to prevent cross contamination of the contents of the wells. When the lid is in position over the multiwell plate, rings 36 should be spaced just above the openings at the top of the wells, but should not prevent the air exchange between the wells and the external environment.

In order to support lid 14 in position on multiwell plate 12, lid pads 38 are provided in each corner of the lid. These pads rest atop rim 27 of the plate and support the lid in proper position during use of the multiwell tissue culture assembly.

Inwardly spaced from skirt 32 and extending downwardly from the bottom surface of cover 31 is a rib 40. This rib, lying substantially parallel to each of the four sides of skirt 32, is positioned on the cover so as to depend downwardly into the recess formed by recessed ledge 22, but remaining out of contact with the ledge. Accordingly, a space 41 remains between rib 40 and ledge 22 when the lid is properly positioned on the multiwell plate, as more clearly illustrated in FIG. 4.

In each of the four corners of lid 14, however, rib 40 is extended downwardly in the form of a flange 42. The flange in each corner essentially has two legs in the shape of the angle at each of the corners. Due to the longer downward extension of flange 42, each flange makes contact with recessed ledge 22 at the corners of the multiwell plate. Thus, both flanges 42 and pads 38 contribute to supporting lid 14 in proper position on multiwell plate 12. In this position, cover 31 is raised over openings 24 of the wells so that a space 44 exists therebetween. Except in the corners where flanges 42 contact recessed ledge 22, spaces 34,35,41 and 44 all communicate with each other so as to provide an air passageway. This passageway allows the air exchange between wells 15 and the external environment. However, and as can be seen in the drawings, the passageway is in a labyrinth form thereby minimizing the airflow between the wells and the external environment. Further, the downwardly depending rib into the recess formed by the recessed ledge of the multiwell plate controls airflow and directs the airflow away from the outer periphery of the multiwell plate.

In the corners of the plate, airflow is blocked off completely due to the contact made by flanges 42 with recessed ledge 22 of the plate. Thus, all of these features and elements of the present lid and plate minimize the evaporation of liquid culture media in the wells, particularly those wells in the corners and the peripheral edges of the plate. Interior wells are not normally affected by the above-described evaporation problem. Furthermore, not only is the media evaporation problem controlled, but the present invention also serves the other main functions of a multiwell tissue culture assembly. Specifically, sterility of the contents of the wells is maintained and adequate air exchange is provided between the wells and the external environment to maintain equilibration therebetween. This is due to the partial blockage of air exchange with respect to the wells and the unique labyrinth passage provided by the cooperating elements of the lid and plate of the present invention.

While the lid and plate of the multiwell tissue culture assembly may be fabricated from many different materials of choice, plastic is preferred. Transparent and rigid plastic, such as polystyrene and the like, is the material of choice for the lid and plate components. It is preferred that the lid and plate be molded, each as an integrally formed, one-piece member.

Thus, the present invention provides a multiwell tissue culture assembly which is a significant improvement over existing tissue culture assemblies. In accordance with the features of the present invention, airflow is restricted to the culture wells via a novel labyrinth air passage route. The restriction of airflow maintains optimum conditions for cell culture procedures, primarily through reduction of media loss through evaporation.

What is claimed is:

1. A multiwell tissue culture assembly comprising a plate and a lid, said plate including:
    a plurality of wells having openings therein for receiving tissue culture media;
    upstanding side walls forming a quadrilateral outside border of said plate; and
    a ledge spaced inwardly of said side walls and extending around said plate between said side walls and said wells the upper portion of said side walls extending to a position raised above said ledge forming a rim surrounding said ledge;
    said lid removably positioned on said plate and including:
    a substantially planar cover extending over said wells;
    a skirt surrounding said cover defining a plurality of corners on said cover and extending downwardly in spaced relation with respect to the side walls of said plate; and
    a plurality of flanges each of said flanges being inwardly spaced from said skirt and extending downwardly from each corner of said cover in contact with the ledge of said plate so that the cover is raised in spaced relation over the openings into said wells and said rim is positioned between said skirt and said flanges;
    whereby during use of said assembly air exchange is permitted between said wells and the external environment by virtue of the spaces between said lid and said plate with said flanges causing a partial blockage of air exchange with respect to the wells thereby minimizing evaporation of media in the wells.

2. The assembly of claim 1 wherein the ledge of said plate is recessed below the openings into said wells.

3. The assembly of claim 2 wherein said lid further includes ribs between said flanges extending downwardly from said cover toward said ledge, but out of contact with said ledge, said flanges extending downwardly a longer distance than said ribs so as to contact said ledge in the corners thereof.

4. The assembly of claim 1 wherein said plate further includes an annular base forming the lower portion of said side walls, said base being stepped outwardly from said side walls to form an annular shoulder between said base and the upper portion of said side walls.

5. The assembly of claim 4 wherein the skirt extends to a position adjacent to, but out of contact with, the shoulder of said plate.

6. The assembly of claim 1 wherein said wells are arranged in substantially orthogonal rows and columns.

7. The assembly of claim 1 wherein said plate and said lid are made of transparent plastic.

8. A multiwell tissue culture assembly comprising a plastic plate and a plastic lid, said plate including:
    a plurality of wells having openings therein for receiving tissue culture media;
    upstanding side walls forming a quadrilateral border of said plate, the lower portion of said side walls being an annular base stepped from the side walls to form an annular shoulder between the base and the upper portion of said side walls;
    a ledge spaced inwardly of said side walls and extending around said plate between the upper portion of said side walls and said wells, said ledge being recessed below the openings into said wells, the upper portion of said side walls extending to a position raised above said ledge forming a rim surrounding said ledge;
    said lid removably positioned on said plate and including:
    a substantially planar cover extending over said wells;
    a skirt surrounding said cover defining a plurality of corners on said cover and extending downwardly in spaced relation with respect to the upper portion of the side walls of said plate and terminating in a position adjacent to, but out of contact with, said annular shoulder of said plate thereby leaving a space therebetween;
    a rib inwardly spaced from said skirt and extending downwardly from the cover toward said ledge, but out of contact in spaced relation with said ledge; and
    a flange extending downwardly from each corner of the cover as a longer extension of the rib in the corners, said flange contacting the ledge of the plate so that the cover is raised in spaced relation over the openings into said wells, whereby during use of said assembly the spaces between said lid and said plate form a labyrinth passage permitting an air exchange between the wells and the external environment and in conjunction with said flanges, said labyrinth passage causes a partial blockage of air exchange with respect to the wells thereby minimizing evaporation of media in the wells.

9. A lid for use in conjunction with a tissue culture plate comprising:
    a substantially planar cover;
    a skirt surrounding said cover defining a plurality of corners on said cover and extending downwardly to form side walls;
    a continuous rib inwardly spaced from said skirt and extending downwardly from the cover; and
    a flange extending downwardly from each corner of the cover as a longer extension of the rib in the corners.

* * * * *